US012643866B2

(12) United States Patent
Fang et al.

(10) Patent No.: US 12,643,866 B2
(45) Date of Patent: Jun. 2, 2026

(54) SMALL MOLECULE COMPOUND SERVING AS JAK KINASE INHIBITOR AND USE THEREOF

(71) Applicant: TECHNODERMA MEDICINES, INC., Chengdu (CN)

(72) Inventors: Wenkui Ken Fang, Chengdu (CN); Guanqun Li, Chengdu (CN); Yuting Cai, Chengdu (CN); Xiang Pan, Chengdu (CN); Wenhao Zhu, Chengdu (CN); Yang Wang, Chengdu (CN); Zengquan Wang, Chengdu (CN)

(73) Assignee: TECHNODERMA MEDICINES INC, Chengdu (CN)

( * ) Notice: Subject to any disclaimer, the term of this patent is extended or adjusted under 35 U.S.C. 154(b) by 501 days.

(21) Appl. No.: 18/248,362

(22) PCT Filed: Sep. 24, 2021

(86) PCT No.: PCT/CN2021/120119
§ 371 (c)(1),
(2) Date: Apr. 7, 2023

(87) PCT Pub. No.: WO2022/073424
PCT Pub. Date: Apr. 14, 2022

(65) Prior Publication Data

US 2023/0373933 A1 Nov. 23, 2023

(30) Foreign Application Priority Data

Oct. 9, 2020 (CN) ......................... 202011072703.7

(51) Int. Cl.
*C07D 239/42* (2006.01)
*C07D 401/04* (2006.01)
*C07D 401/12* (2006.01)
*C07D 401/14* (2006.01)

(52) U.S. Cl.
CPC ......... *C07D 239/42* (2013.01); *C07D 401/04* (2013.01); *C07D 401/12* (2013.01); *C07D 401/14* (2013.01)

(58) Field of Classification Search
CPC .................................................... C07D 239/42
See application file for complete search history.

(56) References Cited

FOREIGN PATENT DOCUMENTS

| | | | | |
|---|---|---|---|---|
| CN | 101421250 | | 4/2009 | |
| CN | 101861313 | | 10/2010 | |
| CN | 102791697 | | 11/2012 | |
| CN | 110627775 | | 12/2019 | |
| CN | 110627775 | A | * 12/2019 | ............. A61P 19/02 |
| CN | 112142675 | | 12/2020 | |
| JP | 2011-503194 | A | 1/2011 | |
| TW | 201737913 | A | 11/2017 | |
| WO | 2004/041789 | | 5/2004 | |
| WO | WO 2009/064835 | A1 | 5/2009 | |
| WO | 2017/007658 | | 1/2017 | |

OTHER PUBLICATIONS

International Search Report with English translation dated Feb. 11, 2022, for PCT/CN2021/120119, 11 pp.
Written Opinion of the ISA dated Feb. 11, 2022, for PCT/CN2021/120119, 5 pp.
First Chinese Office Action with English translation dated Jun. 17, 2021, for CN202011072703.7, 12 pp.
Chinese Office Action with English translation dated Aug. 17, 2021, for CN202011072703.7, 12 pp.
Extended European Search Report mailed Aug. 29, 2024 in European Application No. 21876942.0, 10 pages.

* cited by examiner

*Primary Examiner* — John S Kenyon
*Assistant Examiner* — Rehana Ismail
(74) *Attorney, Agent, or Firm* — Nixon & Vanderhye P.C.

(57) ABSTRACT

Provided in the present invention are a small molecule compound, which is the compound represented by formula (I), or a stereoisomer, a geometric isomer, a tautomer, a hydrate, a solvate, and a pharmaceutically acceptable salt or a prodrug thereof, where $R_1$ to $R_4$ are each independently selected from C or N, and wherein R is selected from a cycloalkyl, substituted cycloalkyl, heterocycloalkyl, substituted heterocycloalkyl, aryl, substituted aryl, heteroaryl or substituted heteroaryl. The small molecule compound of the present disclosure can inhibit a JAK kinase, and more particularly is used as a JAK1/Tyk2 dual inhibitor and a Tyk2 specific inhibitor.

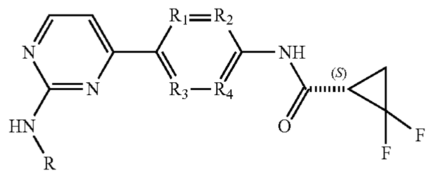

18 Claims, No Drawings

SMALL MOLECULE COMPOUND SERVING AS JAK KINASE INHIBITOR AND USE THEREOF

CROSS-REFERENCE TO RELATED APPLICATIONS

This application is the U.S. national phase of International Application No. PCT/CN2021/120119 filed Sep. 24, 2021 which designated the U.S. and claims priority to CN 202011072703.7 filed Oct. 9, 2020, the entire contents of each of which are hereby incorporated by reference.

TECHNICAL FIELD

The present disclosure relates to the field of small molecule compounds, and in particular to a small molecule compound usable for prevention, treatment, or alleviation of autoimmune diseases such as rheumatic arthritis, ulcerative colitis, and systemic lupus erythematosus; or related inflammatory skin diseases such as psoriasis, eczema, vitiligo, and alopecia areata.

BACKGROUND

JAK (Janus Kinase) is a family of intracellular non-receptor tyrosine protein kinases, including four members: JAK1, JAK2, JAK3 and Tyk2. JAK-STAT (Signal Transducer and Activator of Transcription proteins) signaling pathway is the main pathway for intracellular signaling stimulated by combination of inflammatory cytokines and receptors. Many evidences indicate that the JAK-STAT signaling pathway is indispensable in the pathogenesis of many diseases, especially autoimmune diseases such as rheumatoid arthritis, lupus erythematosus, inflammatory bowel disease, multiple sclerosis, Sjogren's syndrome, psoriasis, alopecia areata, and vitiligo; and allergic diseases such as asthma, allergic rhinitis, allergic conjunctivitis, atopic dermatitis, and eczema. Therefore, inhibiting the activity of JAK kinases, especially that of JAK1 and TYK2 kinases, with highly effective small molecules can block the signaling pathway mediated by cytokines involved in inflammatory responses, thereby controlling inflammations and effectively treating autoimmune diseases and/or allergic inflammatory diseases.

During the pathogenetic processes of different inflammatory diseases, T cells differentiate in different directions depending on different inflammatory inducing factors such as viral or bacterial infections, forming T cell subsets such as Th1, Th2, and Th17. These T cells correspondingly produce different cytokines, for example, Th1 cells related to acute inflammations caused by viral infections produce IFNγ and IL-2, allergy-related Th2 cells produce IL-4, IL-5, and IL-13, and autoimmunity-related Th17 cells produce IL-17, IL-12, IL-21, IL-22, and IL-23. After binding to receptors on cell surfaces, these cytokines transmit inflammatory signals through JAK in the cells and propel the pathological process of the disease. More importantly, the pathogenesis of many inflammatory diseases with unclear etiology is complex and involves multiple T cell subsets at different stages or even at the same stage, that is, multiple JAK pathways are involved, which poses new requirements for the development of medications for treating JAK inflammatory diseases.

Although some studies have reported that JAK1 inhibitors can specifically inhibit Th2 allergic inflammations, there are few reports on inhibitors effectively inhibiting JAK1 and/or TYK2. In particular, it is believed that JAK1/Tyk2 dual inhibitors and Tyk2 inhibitors have broader clinical potential, especially for inflammatory diseases whose pathogenesis involves autoimmune abnormalities. In addition, pathogenesis of more inflammatory diseases, especially inflammatory skin diseases, may involve multiple JAKs, and therefore, to develop potent single or dual inhibitors of JAK1 and Tyk2 is of great significance especially for topical treatment of skin diseases, and potent inhibitors can not only achieve good efficacy, but also avoid side effects caused by systemic medications, but this will also require strong inhibitory activity to achieve.

SUMMARY

The present disclosure aims to obtain highly effective JAK1/Tyk2 dual inhibitors and Tyk2 specific inhibitors to provide targeted treatments for different inflammatory diseases. For example, the JAK1/Tyk2 dual inhibitors may be suitable for diseases such as SLE, vitiligo, IBD, and eczema, and the Tyk2 specific inhibitors may be more suitable for diseases such as rheumatoid arthritis, psoriasis, and alopecia areata, while avoiding hematopoietic inhibition and coagulation abnormalities caused by inhibition of JAK2. In addition, good therapeutic effects can be obtained with the selection of inhibitors of the JAK family that are suitable for topical administration such as topical administration for inflammatory skin diseases, and have various properties associated with the etiology and symptoms of the diseases, for intervention and symptom control.

In order to achieve the above objective, in one aspect, the present disclosure provides a small molecule compound, where the small molecule compound is a compound represented by Formula I below, or a stereoisomer, a geometric isomer, a tautomer, a hydrate, a solvate, a pharmaceutically acceptable salt or a prodrug thereof:

[Formula I]

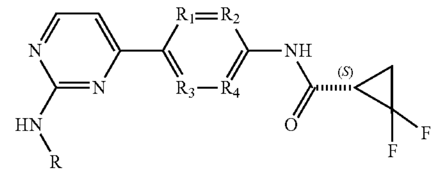

where $R_1$ to $R_4$ are each independently selected from C or N; and where R is selected from a cycloalkyl group, a substituted cycloalkyl group, a heterocycloalkyl group, a substituted heterocycloalkyl group, an aryl group, a substituted aryl group, a heteroaryl group, or a substituted heteroaryl group.

In an embodiment, at most two of $R_1$ to $R_4$ are N.

In another embodiment, R has a structure represented by Formula II below:

[Formula II]

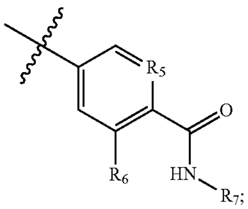

where $R_5$ is selected from C or N;

where $R_6$ is selected from hydrogen, halogen, an alkyl group, an amino group, an amido group, a cycloalkyl group, a heterocycloalkyl group, an aryl group, or a heteroaryl group; and where $R_7$ is selected from hydrogen, an alkyl group, a cycloalkyl group, a heterocycloalkyl group, an aryl group, or a heteroaryl group.

In another embodiment, $R_6$ and $R_7$ are each independently selected from hydrogen, an alkyl group, or a cycloalkyl group.

In another embodiment, R has a structure represented by Formula III below:

[Formula III]

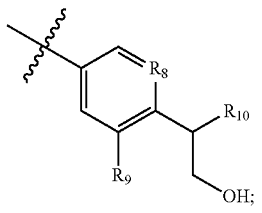

where $R_8$ is selected from C or N;

where $R_9$ is selected from hydrogen, halogen, an alkyl group, an amino group, an amido group, a cycloalkyl group, a heterocycloalkyl group, an aryl group, or a heteroaryl group; and where $R_{10}$ is selected from hydrogen, an alkyl group, a cycloalkyl group, a heterocycloalkyl group, an aryl group, or a heteroaryl group.

In another embodiment, $R_9$ and $R_{10}$ are each independently selected from hydrogen, an alkyl group, or a cycloalkyl group.

In another embodiment, the alkyl group is a methyl group, an ethyl group, a propyl group, or an isopropyl group, and the cycloalkyl group is a cyclopropyl group, a cyclobutyl group, or a cyclopropylmethyl group.

In another aspect, the present disclosure further provides use of the small molecule compound in inhibition of JAK kinase.

In another aspect, the present disclosure further provides use of the small molecule compound in preparation of a medication for prevention or treatment of an autoimmune disease associated with JAK, and an immune-related inflammatory skin disease.

In an embodiment, the autoimmune disease is at least one selected from the group consisting of rheumatoid arthritis, ankylosing spondylitis, ulcerative colitis, Crohn's disease, systemic lupus erythematosus, dermatomyositis, multiple sclerosis, type I diabetes mellitus, Sjogren's syndrome, and vasculitis.

In another embodiment, the immune-related inflammatory skin disease is at least one selected from the group consisting of atopic dermatitis, eczema, alopecia areata, psoriasis, vitiligo, lichen planus, lichen nitidus, lichen sclerosus et atrophicus, panniculitis, acne, and hidradenitis suppurativa.

The present disclosure achieves the following effects:

In the present disclosure, a purposeful and reasonable design of a small molecule compound is conducted based on the protein structure of JAK kinases, especially the protein structure of Tyk2. The synthesized compounds are first subjected to JAK kinase biochemical activity testing, and a SAR (structure-activity relationship) is established based on $IC_{50}$, and potent inhibitors having $IC_{50}$ of 200 nM or less are further subjected to cytological testing to determine the selectivity of the compounds. The specific activity experimental data shows that the compounds according to the present disclosure have good inhibition capabilities for JAK kinase activity and cell biological activity.

DETAILED DESCRIPTION

Specific embodiments of the present disclosure will be described in detail below. It should be understood that the specific embodiments described herein are only intended to illustrate and explain the present disclosure and are not intended to limit the present disclosure.

The endpoints and any value of ranges disclosed herein are not limited to precise ranges or values, and these ranges or values should be understood to include values close to these ranges or values. For numerical ranges, combinations can be made between the endpoint values of each range, between the endpoint values of each range and individual point values, and between individual point values to obtain one or more new numerical ranges, and these numerical ranges should be regarded as being specifically disclosed herein.

Before describing the present disclosure in detail, it should be understood that the terms used herein are only intended to describe specific embodiments and are not intended to limit the scope of the present disclosure, where the scope of the present disclosure is limited only by the appended claims. For a more complete understanding of the present disclosure described herein, the following terms are used, and the definitions of the terms are shown below. Unless otherwise defined, all technical and scientific terms used herein have the same meanings as those understood by persons of ordinary skills in the art to which the present disclosure belongs.

In one aspect, the present disclosure provides a small molecule compound, where the small molecule compound is a compound represented by Formula I below, or a stereoisomer, a geometric isomer, a tautomer, a hydrate, a solvate, a pharmaceutically acceptable salt or a prodrug thereof:

[Formula I]

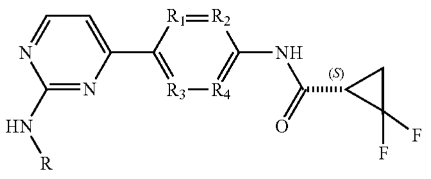

where $R_1$ to $R_4$ are each independently selected from C or N; and where R is selected from a cycloalkyl group, a substituted cycloalkyl group, a heterocycloalkyl group, a substituted heterocycloalkyl group, an aryl group, a substituted aryl group, a heteroaryl group, or a substituted heteroaryl group.

That is, $R_1$, $R_2$ $R_3$, and $R_4$ may be each independently selected from C or N. In a preferable embodiment, at most two (that is, 0, 1, or 2) of $R_1$ to $R_4$ may be N. In another preferable embodiment, at most one (that is, 0 or 1) of $R_1$ to $R_4$ may be N. When at most one (that is, 0 or 1) of $R_1$ to $R_4$ is N, a benzene ring or a pyridine ring is formed.

According to the present disclosure, in a preferable embodiment, R may have a structure represented by Formula II below:

[Formula II)

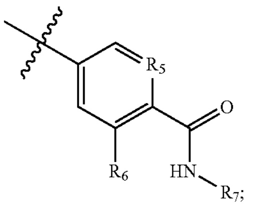

where $R_5$ may be selected from C or N;

where $R_6$ is selected from hydrogen, halogen, an alkyl group, an amino group, an amido group, a cycloalkyl group, a heterocycloalkyl group, an aryl group, or a heteroaryl group; and where $R_7$ is selected from hydrogen, an alkyl group, a cycloalkyl group, a heterocycloalkyl group, an aryl group, or a heteroaryl group.

In a more preferable embodiment, $R_6$ and $R_7$ may be each independently selected from hydrogen, an alkyl group, or a cycloalkyl group, and further, the alkyl group may be a methyl group, an ethyl group, a propyl group, or an isopropyl group, and the cycloalkyl group is a cyclopropyl group, a cyclobutyl group, or a cyclopropylmethyl group.

For example, in a specific embodiment, $R_5$ is C, $R_6$ is hydrogen, and $R_7$ is an ethyl group. In this case, R can have the following structure:

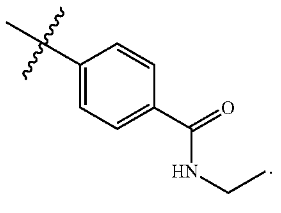 [SMILES: *c1ccc(C(=O)NCC)cc1]

For example, in a specific embodiment, $R_5$ is N, $R_6$ is a methyl group, and $R_7$ is a methyl group. In this case, R can have the following structure:

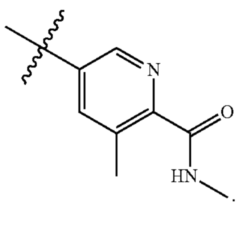 [SMILES: *c1cnc(C(=O)NC)c(C)c1]

For example, in a specific embodiment, $R_5$ is C, $R_6$ is a methyl group, and $R_7$ is an ethyl group. In this case, R can have the following structure:

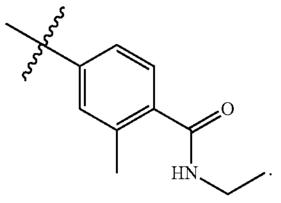 [SMILES: *c1ccc(C(=O)NCC)c(C)c1]

For example, in a specific embodiment, $R_5$ is N, $R_6$ is a methyl group, and $R_7$ is hydrogen. In this case, R can have the following structure:

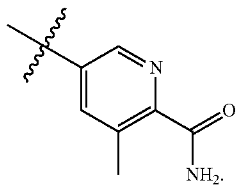 [SMILES: *c1cnc(C(N)=O)c(C)c1]

According to the present disclosure, in another preferable embodiment, R may have a structure represented by Formula III below:

[Formula III]

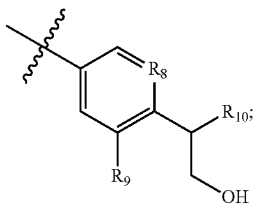

where $R_8$ may be selected from C or N;

where $R_9$ is selected from hydrogen, halogen, an alkyl group, an amino group, an amido group, a cycloalkyl group, a heterocycloalkyl group, an aryl group, or a heteroaryl group; and where $R_{10}$ is selected from hydrogen, an alkyl group, a cycloalkyl group, a heterocycloalkyl group, an aryl group, or a heteroaryl group.

In a more preferable embodiment, $R_9$ and $R_{10}$ may be each independently selected from hydrogen, an alkyl group, or a cycloalkyl group, and further, the alkyl group may be a methyl group, an ethyl group, a propyl group, or an isopropyl group, and the cycloalkyl group is a cyclopropyl group, a cyclobutyl group, or a cyclopropylmethyl group.

For example, in a specific embodiment, $R_8$ is N, $R_9$ is hydrogen, and $R_{10}$ is a methyl group. In this case, R can have the following structure:

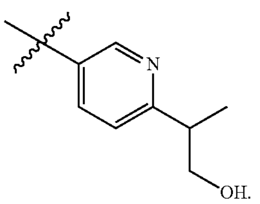 [SMILES: *c1ccc(C(C)CO)nc1]

According to the present disclosure, in another preferable embodiment, R may also have the following structure:

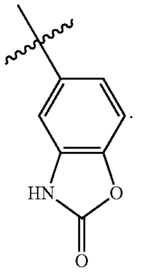 [SMILES: *c1ccc2oc(=O)[nH]c2c1]

As used herein, the term "pharmaceutically acceptable" refers to a substance does not affect biological activity or properties of a compound of the present disclosure, and is relatively non-toxic, that is, the substance can be applied to an individual without causing an adverse biological reaction or having interaction in an adverse manner with any component contained in the composition. In the present disclosure, "a pharmaceutically acceptable salt" may include an inorganic salt and an organic salt, where the organic salt may include, but is not limited to, an ammonium, lithium, sodium, potassium, cesium, calcium, magnesium, copper, aluminum, zinc, barium or quaternary ammonium salt, and the inorganic salt may include, but is not limited to, an arginine, tert-butylamine, dimethylamine, diethanolamine, ethanolamine, ethylenediamine, imidazole, lysine, methylamine, pyridine, picolinate piperazine, triethylamine, triethanolamine, trimethylamine, or urea salt.

In another aspect, the present disclosure provides use of the small molecule compound in inhibition of JAK kinase, in particular as a JAK1/Tyk2 dual inhibitor and a Tyk2 specific inhibitor.

In another aspect, the present disclosure further provides use of the small molecule compound in preparation of a medication for prevention or treatment of an autoimmune disease and an immune-related inflammatory skin disease. Studies show that the pathogenesis of each of the diseases is associated with a disorder in JAK signaling.

As used herein, the term "treatment" refers to any administration of a therapeutic agent according to a therapeutic regimen, where the therapeutic regimen achieves desired effects, that is, partial or complete alleviation, improvement, remission, inhibition, delayed onset, reduction in severity, and/or reduction in the incidence of one or more symptoms or characteristics of a specific disease, disorder, and/or condition; and in some embodiments, the administration of a therapeutic agent according to a therapeutic regimen is associated with achievement of desired effects. Such treatment may be targeted at a subject who does not show a relevant disease, disorder, and/or symptom, and/or a subject who shows only early signs of the disease, disorder and/or condition. Alternatively or additionally, such treatment may be targeted at a subject shows one or more of the identified signs of the relevant disease, disorder, and/or condition. In some embodiments, the treatment may be targeted at a subject who has been diagnosed with the relevant disease, disorder, and/or condition. In some embodiments, the treatment may be targeted at a subject who is known to have one or more predisposing factors that are statistically associated with an increased risk of developing the relevant disease, disorder, and/or condition.

According to the present disclosure, the medication prepared for the above use may include an effective amount of the small molecule compound of the present disclosure, and a pharmaceutically acceptable excipient, carrier, or diluent.

As used herein, the term "effective amount", "therapeutically effective amount", or "pharmaceutically effective amount" refers to an amount of a therapeutic agent that confers a therapeutic effect on a treated subject with an appropriate benefit-risk ratio applicable to any medication. Such a therapeutic effect may be objective (that is, measurable through a specific test or marker) or subjective (that is, the effect is indicated or felt by the subject). In some embodiments, the "therapeutically effective amount" refers to an amount of a therapeutic agent or a composition for effectively treating, improving, or preventing (for example, delaying onset of) a related disease or symptom, and/or conferring a detectable therapeutic or prophylactic effect by improving a symptom associated with a disease, preventing or delaying the onset of the disease, and/or also reducing severity or frequency of the symptom.

A person skilled in the art should understand that the therapeutically effective amount of the small molecule compound to be administered will vary depending on the following: the subject and the nature and severity of the disease, the physical condition of the subject, the treatment regimen (for example, whether a second therapeutic agent is used), and the selected route of administration; and an appropriate dose can be readily determined by a person skilled in the art. Additionally, the optimal amount and the interval of individual doses will be determined depending on the nature and severity of the condition being treated, the form, route, and location of administration, as well as the age and condition of the specific subject being treated, and the appropriate dose to be administered will finally be determined by the physician. The dose can be repeated multiple times as needed. If a side effect occurs, the amount and/or frequency of the dose can be changed or reduced in accordance with normal clinical practice.

In the present disclosure, the "pharmaceutically acceptable excipient, carrier, or diluent" includes, but is not limited to, any adjuvant, carrier, excipient, glidant, sweetener, diluent, preservative, dye/colorant, flavoring agent, surfactant, wetting agent, dispersant, suspending agent, stabilizer, isotonic agent, solvent, emulsifier, or the like approved for use in humans or livestock by relevant regulatory authorities.

According to the present disclosure, in addition to the small molecule compound of the present disclosure as an effective ingredient, the medication prepared for the above use may further include a formulation as an additional effective ingredient for prevention or treatment of an autoimmune disease and an immune-related inflammatory skin disease. Examples of such a formulation include, but are not limited to, vitamin D derivatives, vitamin A derivatives, glucocorticoids, calcineurin inhibitors, or non-steroidal anti-inflammatory drugs. When the medication contains a plurality of effective ingredients, each effective ingredient may be administered simultaneously, sequentially, or separately at the discretion of the physician.

In addition, the small molecule compound of the present disclosure can be administered to a patient through various routes, for example, oral, transdermal, subcutaneous, intranasal, intravenous, intramuscular, intrathecal, regional, or topical (for example, mucosa) route. The most appropriate route of administration in any given situation depends on the subject and the nature and severity of the disease, the physical conditions of the subject, and the like. In an embodiment, the small molecule compound of the present disclosure may be administered intravenously. In another embodiment, the small molecule compound of the present disclosure may be administered orally. Correspondingly, the medication of the present disclosure can be prepared into different dosage forms according to different routes of administration. For example, in an embodiment, the medication may be prepared as a tablet, a capsule, a pill, a granule, an aerosol, a spray, or an injection.

According to the research of the inventors, the small molecule compound and the medication prepared therefrom in the present disclosure can have an excellent effect in the prevention or treatment of JAK-related autoimmune diseases and immune-related inflammatory skin diseases. Specifically, the autoimmune diseases may include, but are not limited to, rheumatoid arthritis, ankylosing spondylitis, ulcerative colitis, Crohn's disease, systemic lupus erythematosus, dermatomyositis, multiple sclerosis, type I diabetes mellitus, Sjogren's syndrome, and vasculitis; and the immune-related inflammatory skin diseases may include, but are not limited to, atopic dermatitis, eczema, alopecia areata, psoriasis or vitiligo, lichen planus, lichen nitidus, lichen sclerosus et atrophicus, panniculitis, acne, and hidradenitis suppurativa.

The effects of specific small molecule compounds of the present disclosure will be described in detail through examples below.

EXAMPLES

Example 1: General Method for Synthesizing Compound 1 (TDM-180972)

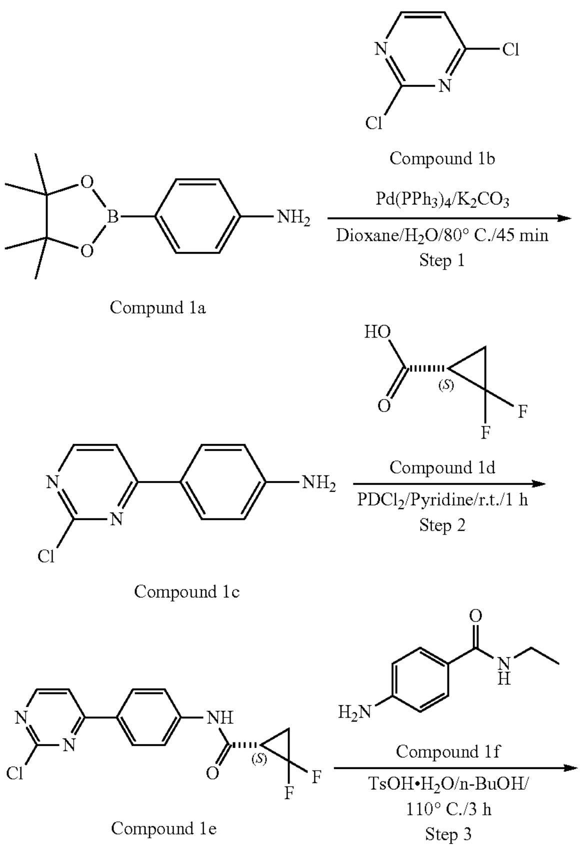

-continued

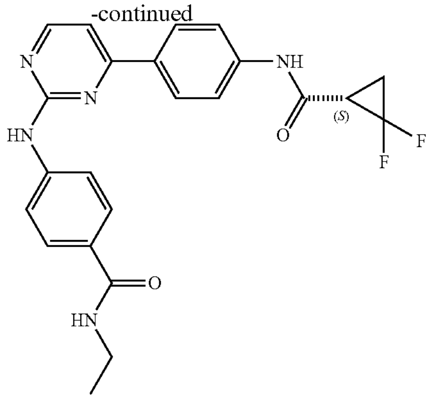

Compound 1

Step 1: Preparation of Compound 1c (4-(2-chloropyrimidin-4-yl)aniline)

Compound 1a (2 g, 9.129 mmol), compound 1b (1.36 g, 9.129 mmol), tetrakis(triphenylphosphine)palladium (527 g, 0.45 mmol), potassium carbonate (2.5 g, 18.258 mmol), dioxane (20 mL), and water (20 mL) were added into a three-necked flask, and nitrogen displacement was conducted several times, and then the mixture was heated to 80° C. and stirred for 45 minutes. After the reaction ended, the reactants were concentrated under reduced pressure, and the residue was purified by silica gel chromatography (petroleum ether/ethyl acetate=0%-60%) to obtain a target compound (compound 1c, 394 mg, yield: 21%) as a pale yellow solid. LCMS $[M+1]^+$=206.

Step 2: Preparation of Compound 1e ((S)-N-(4-(2-chloropyrimidin-4-yl)phenyl)-2,2-difluorocyclopropane-1-carboxamide)

Compound 1c (300 mg, 1.459 mmol) and compound 1d (187 mg, 1.531 mmol) were added into a three-necked flask, nitrogen displacement was conducted for the mixture several times, and then pyridine (10 mL) and phosphorus oxychloride (335.6 mg, 2.189 mmol) were added at 0° C. The mixture was stirred at room temperature for 1 hour, and then concentrated under reduced pressure, the residue was extracted with ethyl acetate (30 mL*3), the organic layers were combined, washed with water (50 mL*3) and saturated brine (50 mL*2), and dried over sodium sulfate, the filtrate was concentrated under reduced pressure, and the residue was purified by silica gel chromatography (petroleum ether/ethyl acetate=0%-12%) to obtain the target compound (compound 1e, 327.7 mg, yield: 72.5%) as a yellow solid. LCMS$[M+H]^+$=310.

Step 3: Preparation of Compound 1 ((S)-4-((4-(4-(4-(2,2-difluorocyclopropane-1-carboxamido)phenyl)pyrimidin-2-yl)amino)-N-ethylbenzamide)

Compound 1f (85 mg, 0.517 mmol) and p-toluenesulfonic acid monohydrate (98 mg, 0.517 mmol) were added to a solution of compound 1e (80 mg, 0.258 mmol) in n-butanol (8 mL). The resulting mixture was heated to 110° C. and stirred for 3 hours. After the reaction ended, the mixture was concentrated under reduced pressure, and the residue was purified via preparative HPLC (formic acid), to obtain a target compound TDM-180972 (compound 1, 19.7 mg, yield: 17.5%) as a yellow solid. LCMS$[M+H]^+$=438.2.

$^1$H NMR (400 MHz, DMSO) δ10.70 (s, 1H), 9.91 (s, 1H), 8.57 (d, J=5.3 Hz, 1H), 8.28 (t, J=5.5 Hz, 1H), 8.19 (d, J=8.8 Hz, 2H), 7.92 (d, J=8.9 Hz, 2H), 7.83 (d, J=8.9 Hz, 2H), 7.78 (d, J=8.8 Hz, 2H), 7.44 (d, J=5.3 Hz, 1H), 3.28 (dt, J=12.7, 6.4 Hz, 2H), 2.86 (ddd, J=13.6, 10.8, 8.0 Hz, 1H), 2.12-1.94 (m, 2H), 1.13 (t, J=7.2 Hz, 3H).

Example 2: General Method for Synthesizing Compound 2 (TDM-180974)

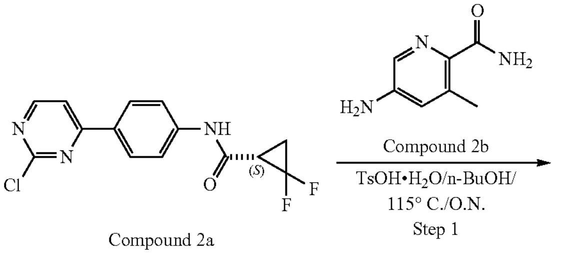

Compound 2a

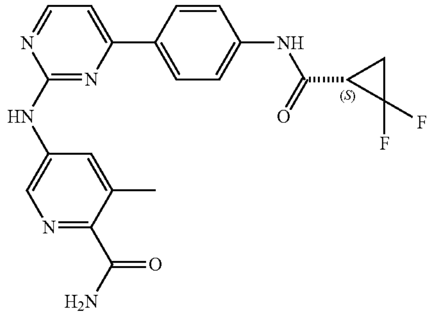

Compound 2

Step 1: Preparation of Compound 2 ((S)-5-((4-(4-(4-(2,2-difluorocyclopropane-1-carboxamido)phenyl)pyrimidin-2-yl)amino)-3-methylpyridoline)

Compound 2b (78 mg, 0.517 mmol) and p-toluenesulfonic acid monohydrate (98 mg, 0.517 mmol) were added to a solution of compound 2a (80 mg, 0.258 mmol) in n-butanol (8 mL), and the mixture was heated to 115° C. and stirred overnight. After the reaction ended, the mixture was concentrated under reduced pressure, methanol was added to the residue, a solid was collected by filtration, and the solid was purified via preparative HPLC (formic acid), to obtain a target compound TDM-180974 (compound 2, 18.9 mg, yield: 10.6%) as a white solid. LCMS$[M+H]^+$=425.2.

$^1$H NMR (400 MHz, DMSO) δ10.73 (s, 1H), 10.08 (s, 1H), 8.89 (d, J=2.2 Hz, 1H), 8.60 (d, J=5.3 Hz, 1H), 8.23 (d, J=2.0 Hz, 1H), 8.18 (d, J=8.8 Hz, 2H), 7.90 (s, 1H), 7.79 (d, J=8.8 Hz, 2H), 7.49 (d, J=5.3 Hz, 1H), 7.26 (s, 1H), 2.87 (ddd, J=13.6, 10.8, 8.1 Hz, 1H), 2.61 (s, 3H), 2.10-1.96 (m, 2H).

Example 3: General Method for Synthesizing Compound 3 (TDM-180977)

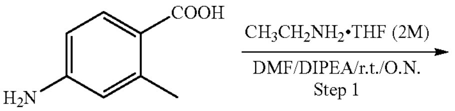

Compound 3a

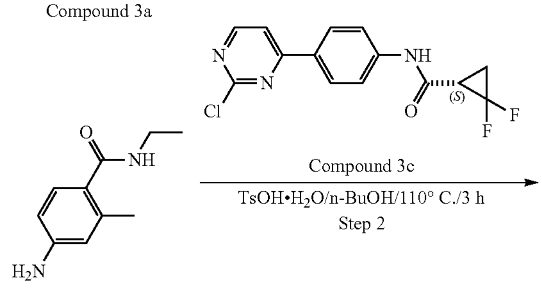

Compound 3b

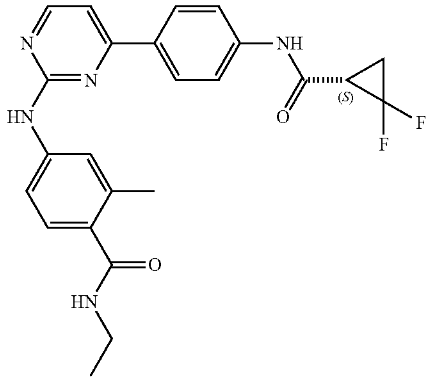

Compound 3

Step 1: Preparation of Compound 3b (4-amino-N-ethyl-2-methylbenzamide)

2-(7-azabenzotriazole)-N,N,N',N'-tetramethyluronium hexafluorophosphate (5.4 g, 14.289 mmol) and N,N-diisopropylethylamine (3.8 g, 29.775 mmol) were added to a solution of compound 3a (1.8 g, 11.91 mmol) in N,N-dimethylformamide (80 mL), the mixture was stirred for 5 minutes, then a solution of ethylamine in tetrahydrofuran (2M) (9 mL, 18 mmol) was added, and the mixture was stirred overnight at room temperature. The mixture was concentrated under reduced pressure to remove some solvent, water was added to the residue, and the residue was extracted with ethyl acetate (100 mL*3), the organic phases were combined, washed with water (150 mL*3) and saturated brine (150 mL), and dried over sodium sulfate, and the filtrate was concentrated under reduced pressure and purified by silica gel chromatography (petroleum ether/ethyl acetate=0%-50%) to obtain a target compound (compound 3b, 1.32 g, yield: 62.2%) as a yellow oil. LCMS$[M+1]^+$=179.

Step 2: Preparation of Compound 3 ((S)-4-(4-(4-(4-(2,2-difluorocyclopropane-1-carboxamido)phenyl)pyrimidin-2-yl)amino)-N-ethyl-2-methylbenzamide)

Compound 3b (92 mg, 0.517 mmol) and p-toluenesulfonic acid monohydrate (98 mg, 0.517 mmol) were added to a solution of compound 3c (80 mg, 0.258 mmol) in n-butanol (8 mL). The resulting mixture was heated to 110° C. and stirred for 3 hours. After the reaction ended, the mixture was concentrated under reduced pressure, and the residue was purified via preparative HPLC (formic acid), to obtain a target compound TDM-180977 (compound 3, 19.4 mg, yield: 13.3%) as a white solid. LCMS$[M+H]^+$=425.2.

$^1$H NMR (400 MHz, DMSO) δ10.70 (s, 1H), 9.72 (s, 1H), 8.54 (d, J=5.3 Hz, 1H), 8.18 (d, J=8.8 Hz, 2H), 8.08 (d, J=5.6 Hz, 1H), 7.81-7.67 (m, 4H), 7.40 (d, J=5.3 Hz, 1H), 7.32 (d, J=8.4 Hz, 1H), 3.28-3.17 (m, 2H), 2.86 (ddd, J=13.6, 10.8, 8.1 Hz, 1H), 2.37 (s, 3H), 2.14-1.93 (m, 2H), 1.11 (t, J=7.2 Hz, 3H).

Example 4: General Method for Synthesizing Compound 4 (TDM-180981)

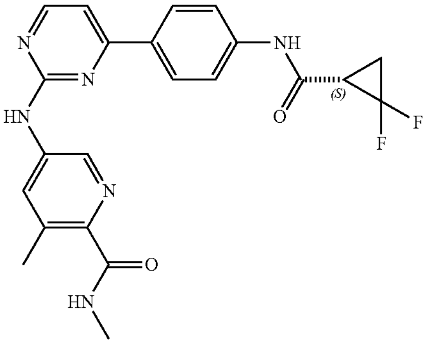

Step 1: Preparation of Compound 4 ((S)-5-((4-(4-(4-(2,2-difluorocyclopropane-1-carboxamido)phenyl)pyrimidin-2-yl)amino)-N,3-dimethylpyridinolineamide)

Compound 4 (white solid, 3.5 mg, yield: 1.6%) was prepared in a method similar to that in Example 3.

$^1$H NMR (400 MHz, DMSO) δ10.74 (s, 1H), 10.06 (s, 1H), 8.92 (d, J=2.2 Hz, 1H), 8.60 (d, J=5.3 Hz, 1H), 8.48 (d, J=4.8 Hz, 1H), 8.22-8.18 (m, 2H), 8.17 (s, 1H), 7.78 (d, J=8.8 Hz, 2H), 7.49 (d, J=5.3 Hz, 1H), 2.87 (ddd, J=13.6, 10.8, 8.0 Hz, 1H), 2.78 (d, J=4.8 Hz, 3H), 2.61 (s, 3H), 2.03 (ddd, J=18.1, 11.7, 6.0 Hz, 2H). LCMS$[M+H]^+$=439.2.

Example 5: General Method for Synthesizing Compound 5 (TDM-180989)

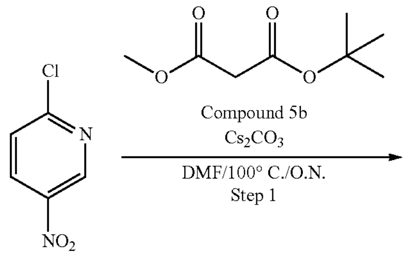

Compound 5a

-continued

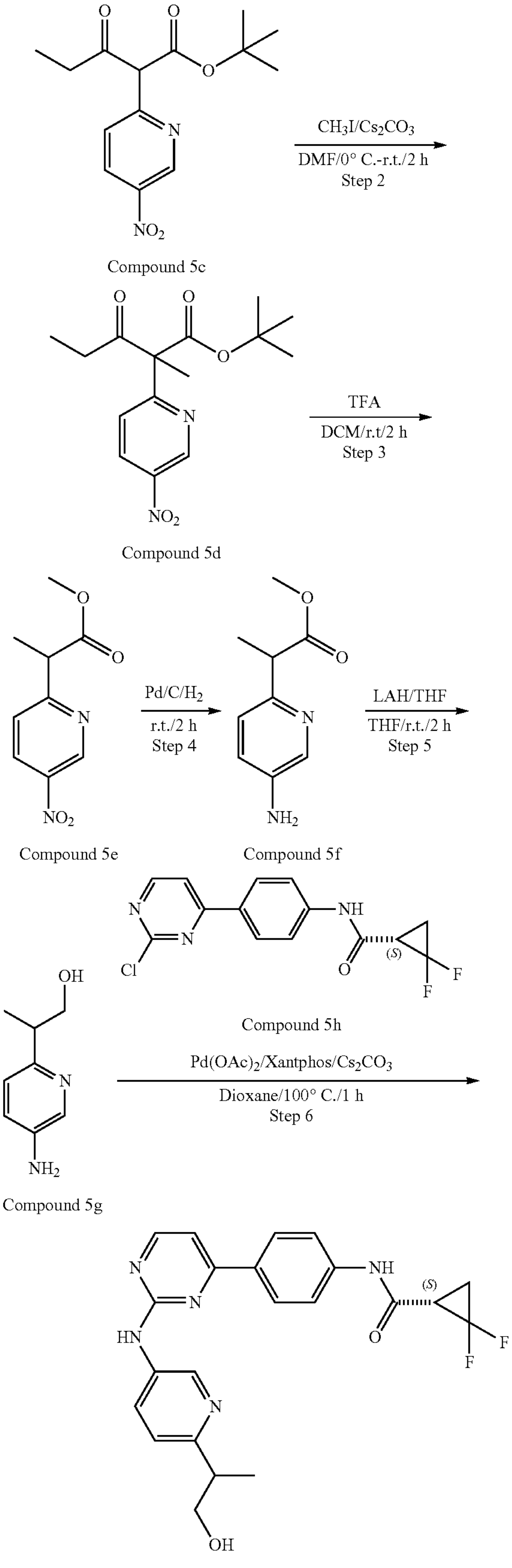

Compound 5

Step 1: Preparation of Compound 5c (1-(tert-butyl) 3-methyl 2-(5-nitropyridin-2-yl) malonate)

Potassium carbonate (17.435 g, 126.152 mmol) and compound 5b (13.185 g, 75.691 mmol) were added to a solution of compound 5a (10 g, 63.076 mmol) in N,N-dimethylformamide (100 mL) at room temperature, and nitrogen displacement was conducted for the mixture several times. The mixture was heated to 100° C. and stirred overnight. After the reaction ended, the mixture was cooled to room temperature, then saturated ammonium chloride solution (150 mL) was added, the mixture was filtered, the filtrate was extracted with ethyl acetate (300 mL*3), the organic layers were combined, washed with saturated brine (200 mL*2), and dried over sodium sulfate, the filtrate was concentrated under reduced pressure, and the residue was purified by silica gel chromatography (petroleum ether/ethyl acetate=0%-6%) to obtain the target compound (compound 5c, 7.286 g, yield: 39%) as a yellow oil. LCMS$[M-C_4H_9]^+$=241.1.

Step 2: Preparation of Compound 5d (1-(tert-butyl) 3-methyl-2-methyl-2-(5-nitropyridin-2-yl)malonate)

Cesium carbonate (15.4 g, 47.252 mmol) was added to a solution of compound 5c (7 g, 23.626 mmol) in N,N-dimethylformamide (150 mL) at 0° C. The mixture was then warmed to room temperature and stirred for 10 minutes, iodomethane (13.4 g, 94.505 mmol) was added, and the mixture was stirred at room temperature for 3 hours. After the reaction ended, water (150 mL) was added to the mixture at 0° C., the mixture was extracted with ethyl acetate (150 mL*3), organic layers were combined, washed with saturated brine (250 mL*2), and dried over sodium sulfate, the filtrate was concentrated under reduced pressure, and the residue was purified by silica gel chromatography (petroleum ether/ethyl acetate=0%-3%) to obtain the target compound (compound 5d, 6.026 g, yield: 82.2%) as a yellow oil. LCMS$[M-C_4H_9]^+$=255.1.

Step 3: Preparation of compound 5e (propyl 2-(5-nitropyridin-2-yl) propionate)

Trifluoroacetate (50 mL) was added to a solution of the compound 5d (6 g, 19.366 mmol) in dichloromethane (150 mL). The mixture was stirred for 3 hours at room temperature. After the reaction ended, the mixture was concentrated under reduced pressure, and the residue was purified by silica gel chromatography (petroleum ether/ethyl acetate=0%-6%) to obtain a target compound (compound 5e, 3.671 g, yield: 90.3%) as a yellow oil. LCMS$[M+1]^+$=211.1.

Step 4: Preparation of Compound 5f (methyl 2-(5-aminopyridin-2-yl) propionate)

An appropriate amount of palladium on carbon was added to a solution of compound 5e (3.67 g, 17.460 mmol) in methanol (120 mL) at room temperature, hydrogen displacement was conducted for the mixture several times, and the mixture was then stirred at room temperature for 2 hours. After the reaction ended, the mixture was filtered, the filtrate was concentrated under reduced pressure, and the residue was purified by silica gel chromatography [petroleum ether/ethyl acetate=0%-50%] to obtain a target compound (compound 5f, 2.6025 g, yield: 82.7%) as a yellow oil. LCMS $[M+1]^+$=181.

Step 5: Preparation of Compound 5g (2-(5-aminopyridin-2-yl)propan-1-ol)

Air in a 100 mL three-necked flask was replaced with nitrogen, lithium aluminum hydride (1.8 g, 47.26 mmol) was added under ice bath, then tetrahydrofuran (180 mL) was added dropwise, and then a solution of compound 5f (1.31 g, 7.27 mmol) in tetrahydrofuran (20 mL) was added. The reactant solution was warmed to room temperature and stirred for 2 hours. After the reaction ended, the reactant solution was cooled in an ice bath, and 1.8 mL of water, 1.8 mL of 15% aqueous sodium hydroxide solution and 5.4 mL of water were added dropwise in sequence. The mixture was filtered to obtain a filtrate, and the filter cake was washed with ethyl acetate. The filtrate was dried over anhydrous sodium sulfate, filtered and concentrated to obtain the target compound (compound 5g, 1.2 g, yield: 95%) as a yellow oil. LCMS $[M+1]^+$=153.

Step 6: Preparation of Compound 5 ((1S)-2,2-difluoro-N-(4-(2-((6-(1-(1-hydroxypropan-2-yl)pyridin-3-yl)amino)pyrimidin-4-yl)phenyl)cyclopropane-1-carboxamide)

Dioxane (25 mL) was added to a mixture of compound 389h (100 mg, 0.323 mmol), compound 389g (98 mg, 0.646 mmol), palladium acetate (7.3 mg, 0.032 mmol), 4,5-bis (diphenylphosphine)-9,9-dimethylxanthene (37.4 mg, 0.065 mmol) and cesium carbonate (316 mg, 0.969 mmol), argon displacement was conducted for the mixture several times, and the mixture was heated to 100° C. and stirred for 1 hour. After the reaction ended, water (30 mL) was added to the reaction mixture, the reaction mixture was extracted with ethyl acetate (30 mL*3), organic layers were combined, washed with water (60 mL) and saturated brine (60 mL), and dried over sodium sulfate, the filtrate was concentrated under reduced pressure, and the residue was purified by preparative HPLC (formic acid) to obtain the target compound TDM-180989 (compound 5, 30.3 mg, yield: 18.4%) as a pale yellow solid. LCMS$[M+H]^+$=426.1.

$^1H$ NMR (400 MHz, DMSO) δ10.70 (s, 1H), 9.71 (s, 1H), 8.86 (d, J=2.5 Hz, 1H), 8.52 (d, J=5.3 Hz, 1H), 8.20-8.10 (m, 3H), 7.77 (d, J=8.8 Hz, 2H), 7.39 (d, J=5.3 Hz, 1H), 7.22 (d, J=8.5 Hz, 1H), 4.60 (s, 1H), 3.64 (dd, J=10.3, 6.6 Hz, 1H), 3.50 (dd, J=10.3, 7.0 Hz, 1H), 2.98-2.81 (m, 2H), 2.13-1.94 (m, 2H), 1.20 (d, J=7.0 Hz, 3H).

Example 6: General Method for Synthesizing Compound 6 (TDM-180971)

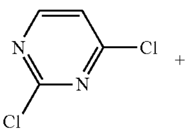

Compound 6a

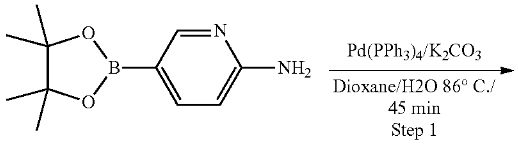

Compound 6b

-continued

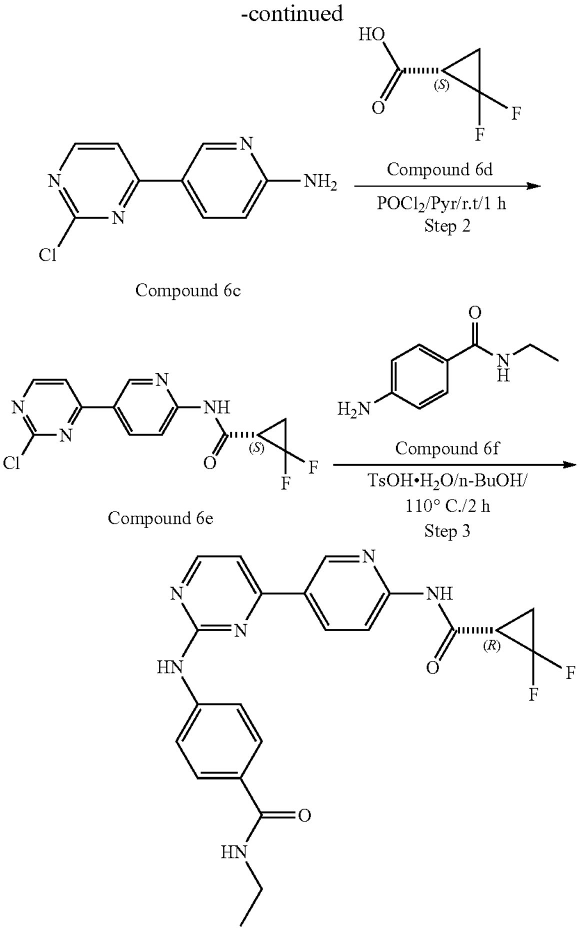

Compound 6c

Compound 6e

Compound 6

Step 1: Preparation of Compound 6c (5-(2-chloropyrimidin-4-yl)pyridin-2-amine)

Compound 6a (1.5 g, 10 mmol), compound 6b (2.21 g, 1.01 mmol), tetrakis(triphenylphosphine)palladium (1.16 g, 1 mmol), potassium carbonate (2.76 g, 20 mmol), 1,4-dioxane (60 mL) and water (60 mL) were added to a 250 mL three-necked flask, nitrogen displacement was conducted for the reactant solution several times, and the reactant solution was heated to 80° C. and stirred for 45 minutes, where LCMS $[M+H]^+$=227, and the reaction was monitored until it completed. Post-treatment: The reactant solution was concentrated and dried, and an obtained crude product was passed through a chromatography column [eluent: (EA/PE) =0%-70%] to obtain a target compound (compound 6c, 1.47 g, yield: 71.36%) as a yellow solid, where LCMS $[M+1]^+$ =207.

Step 2: Preparation of Compound 6e ((S)-N-(5-(2-chloropyrimidin-4-yl)pyridin-2-yl)-2,2-difluorocyclopropane-1-carboxamide)

Compound 6d (910 mg, 7.47 mmol) and phosphorus oxychloride (1.64 g, 10.67 mmol) were added to a solution of compound 6c (1.47 g, 7.11 mmol) in anhydrous pyridine (50 mL). The reactant solution was stirred for 1 hour at room temperature, where LCMS$[M+H]^+$=311, and the reaction was monitored until it completed. Post-treatment: The reactant solution was concentrated and dried, the residue was extracted three times with water and ethyl acetate (3*100 mL), the organic phases were combined, washed with saturated brine, dried over anhydrous sodium sulfate, filtered, concentrated, and dried, the obtained crude product was passed through a chromatography column, [eluent: (EA/PE) =0%-30%], and the crude product was recrystallized to obtain the target compound (compound 6e, 1.73 g, yield: 78.6%) as a yellow solid, where LCMS$[M+H]^+$=311.

Step 3: Preparation of Compound 6 ((S)-4((4-(6-(2,2-difluorocyclopropane-1-formamido)pyridin-3-yl) pyrimidin-2-yl)amino)-N-ethyl benzamide)

Compound 6f (105.7 mg, 0.64 mmol) and p-toluenesulfonic acid monohydrate (122.5 mg, 0.64 mmol) were added to a solution of compound 6e (100 mg, 0.32 mmol) in n-butanol (10 mL). The reactant solution was heated to 110° C. and stirred for 2 hours, where LCMS$[M+H]^+$=439, and the reaction was monitored until it completed. Post-treatment: The reactant solution was concentrated and dried, to obtain a target compound (compound 6, 12.3 mg, yield: 8.7%) as a yellow solid, where LCMS $[M+H]^+$=439.2.

$^1$H NMR (400 MHz, DMSO) δ11.30 (s, 1H), 9.99 (s, 1H), 9.25-9.06 (m, 1H), 8.62 (d, J=5.2 Hz, 1H), 8.57 (dd, J=8.8, 2.4 Hz, 1H), 8.34-8.17 (m, 2H), 7.90 (d, J=8.9 Hz, 2H), 7.82 (d, J=8.9 Hz, 2H), 7.53 (d, J=5.2 Hz, 1H), 3.28 (dt, J=12.7, 6.4 Hz, 2H), 3.04 (dd, J=8.8, 5.7 Hz, 1H), 2.12-1.98 (m, 2H), 1.13 (t, J=7.2 Hz, 3H).

Example 7: General Method for Synthesizing Compound 7 (TDM-180979)

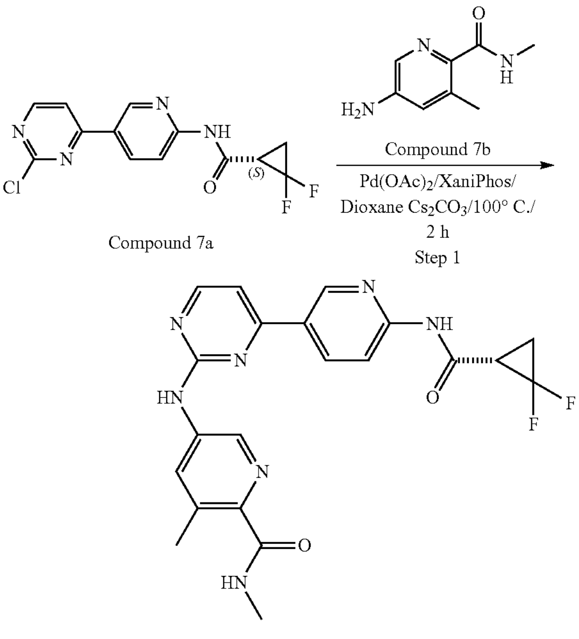

Compound 7a

Compound 7

Step 1: Preparation of Compound 7 ((S)-5((4-(6-(2,2-difluorocyclopropane-1-carboxamido)pyridin-3-yl) pyrimidin-2-yl)amino)-N,3-dimethylpyridinolineamide)

Compound 7b (106.3 mg, 0.64 mmol), palladium acetate (3.6 mg, 0.02 mmol), 4,5-bis(diphenylphosphine)-9,9-dimethylxanthene (18.6 mg, 0.03 mmol) and cesium carbonate (314.7 mg, 0.97 mmol) were added to a solution of compound 7a (100 mg, 0.32 mmol) in dioxane (25 mL). Argon displacement was conducted for the reactant solution several times, the reactant solution was heated to 100° C. and stirred for 2 hours, where LCMS$[M+H]^+$=440, and the reaction was monitored until it completed. Post-treatment: The reaction solution was concentrated to be dried, the residue was slurried with methanol, to obtain a crude product of a target compound (compound 7, 6.4 mg, yield: 3.2%) as a yellow solid, where LCMS $[M+1]^+$=440.0.

$^1$H NMR (400 MHz, DMSO) δ11.34 (s, 1H), 10.15 (s, 1H), 9.17 (d, J=2.0 Hz, 1H), 8.87 (d, J=2.2 Hz, 1H), 8.65 (d, J=5.2 Hz, 1H), 8.56 (dd, J=8.8, 2.4 Hz, 1H), 8.50 (d, J=4.8 Hz, 1H), 8.30-8.18 (m, 2H), 7.58 (d, J=5.3 Hz, 1H), 3.04 (dd, J=8.9, 3.5 Hz, 1H), 2.77 (d, J=4.8 Hz, 3H), 2.61 (s, 3H), 2.05 (dt, J=10.7, 5.2 Hz, 2H).

Example 8: General Method for Synthesizing Compound 8 (TDM-180980)

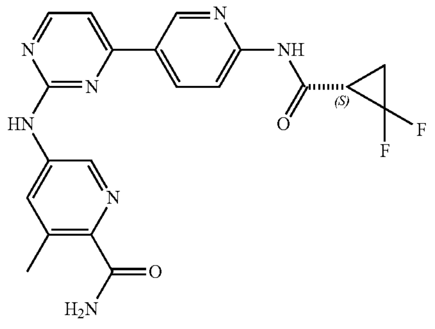

Step 1: Preparation of Compound 8 ((S)-5-((4-(6-(2,2-difluorocyclopropane-1-carboxamido)pyridin-3-yl)pyrimidin-2-yl)amino)-3-methyl pyridinolin-eamide)

Compound 8 (2.3 mg, yellow solid, yield: 1.2%) was prepared in a similar method.

$^1$H NMR (400 MHz, DMSO) δ11.35 (s, 1H), 10.16 (s, 1H), 9.18 (d, J=2.0 Hz, 1H), 8.84 (d, J=2.2 Hz, 1H), 8.66 (d, J=5.2 Hz, 1H), 8.56 (dd, J=8.8, 2.4 Hz, 1H), 8.25 (dd, J=8.2, 5.5 Hz, 2H), 7.90 (s, 1H), 7.58 (d, J=5.3 Hz, 1H), 7.25 (s, 1H), 3.13-2.94 (m, 1H), 2.61 (s, 3H), 2.06 (d, J=9.6 Hz, 2H). LCMS$[M+H]^+$=426.1.

Example 9: General Method for Synthesizing Compound 9 (TDM-180984)

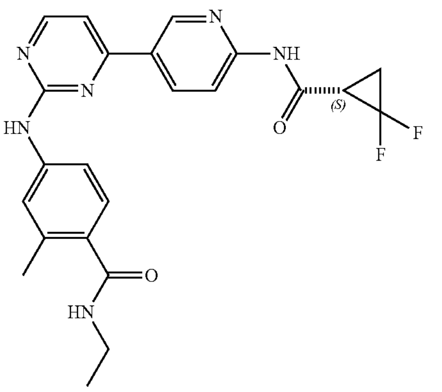

Step 1: Preparation of Compound 9 ((S)-4-((4-(6-(2,2-difluorocyclopropane-1-carboxamido)pyridin-3-yl)pyrimidin-2-yl)amino)-N-ethyl-2-methylbenzamide)

Compound 9 (26.6 mg, yellow solid, yield: 13.04%) was prepared in a similar method.

$^1$H NMR (400 MHz, DMSO) δ11.33 (s, 1H), 9.80 (s, 1H), 9.17 (d, J=1.8 Hz, 1H), 8.68-8.49 (m, 2H), 8.22 (d, J=8.7 Hz, 1H), 8.09 (t, J=5.6 Hz, 1H), 7.80-7.61 (m, 2H), 7.50 (d, J=5.2 Hz, 1H), 7.32 (d, J=8.4 Hz, 1H), 3.28-3.19 (m, 2H), 3.04 (dt, J=13.5, 9.8 Hz, 1H), 2.37 (s, 3H), 2.12-2.00 (m, 2H), 1.11 (t, J=7.2 Hz, 3H). LCMS$[M+H]^+$=453.2.

Example 10: General Method for Synthesizing Compound 10 (TDM-180987)

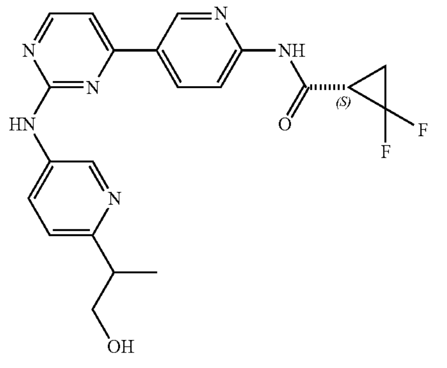

Step 1: Preparation of Compound 10 ((1S)-2,2-difluoro-N-(5-(2-((6-(1-(hydroxypropan-2-yl)pyridin-3-yl)amino)pyrimidin-4-yl)pyridin-2-yl-cyclopropane-1-carboxamide)

Compound 10 (79 mg, off-white solid, yield: 27.8%) was prepared in a similar method.

$^1$H NMR (400 MHz, DMSO) δ11.30 (s, 1H), 9.79 (s, 1H), 9.13 (d, J=2.1 Hz, 1H), 8.84 (d, J=2.5 Hz, 1H), 8.65-8.46 (m, 2H), 8.30-8.07 (m, 2H), 7.48 (d, J=5.2 Hz, 1H), 7.22 (d,

J=8.5 Hz, 1H), 4.59 (t, J=5.3 Hz, 1H), 3.71-3.43 (m, 2H), 3.04 (dt, J=13.5, 9.9 Hz, 1H), 2.91 (dt, J=14.0, 7.0 Hz, 1H), 2.13-1.95 (m, 2H), 1.20 (d, J=6.9 Hz, 3H). LCMS$[M+H]^+$=427.1.

Test Example 1: Detection of Enzyme Activity Inhibition of Small Molecule Inhibitors of JAK Kinases Experimental Scheme 1. Reagent Preparation Kinase reaction buffer: The kinase reaction buffer was prepared with the following components: 50 mM HEPES, pH 7.5, 1 mM EGTA, 10 mM $MgCl_2$, 2 mM DTT, and 0.01% Tween20. 1× test buffer: A test buffer was prepared, and the 10× test buffer was diluted with deionized water (deionized water: test buffer=9:1) to obtain the 1× test buffer. 4× kinase solution: JAK kinase was diluted with a kinase reaction buffer to a final concentration of 4× (JAK1:80 nM, JAK2/JAK3/Tyk2:4 nM). 4× substrate solution: ULight™-JAK (Tyr1023) substrate was diluted with the kinase reaction buffer to 200 nM (final concentration: 50 nM). 4×ATP solution: ATP was diluted with the kinase reaction buffer to a final concentration of 4× (JAK1:160 μM, JAK2/JAK3/Tyk2: 40 μM). 4× test compound solution: The compounds to be tested were dissolved in DMSO to prepare 10 mM stock solutions, which were diluted to have the desired concentrations through 3-fold gradient dilution, 10 concentrations were set for each compound, and final concentrations of the test compounds ranged from 10 μM to 0.5 nM. 4× enzyme reaction termination solution: EDTA was dissolved in a 1× test buffer to 40 mM (final concentration of EDTA: 10 mM). 4× test antibody solution: Eu-labeled test antibodies (anti-phosphotyrosine (PT66)) were diluted with 1× test buffer to 8 nM (final concentration of the antibodies: 2 nM).

2. Test Procedure 2.5 μL of the 4× kinase solution and 2.5 μL of each of the 4× test compound solutions having different concentrations were added into a 384-well microwell plate sequentially, with 2 duplicate wells set for each concentration, and an enzyme solution blank control group and a negative control group (DMSO group) were also provided. The 384-well plate was oscillated to mix the enzyme and the compound uniformly, centrifuged at 1000 rpm for 1 minute, and incubated at room temperature for 60 minutes. 2.5 μL of the 4× substrate solution was added into the 384-well plate, and centrifuged at 1000 rpm for 1 minute. 2.5 μL of the 4×ATP solution was added into the 384-well plate, and centrifuged at 1000 rpm for 1 minute to start the enzyme reaction. JAK1 reacted at room temperature for 2 hours, and JAK2/JAK3/Tyk2 reacted at room temperature for 1 hour. The final concentration of each component in the JAK1 reaction was: JAK1:20 nM; substrate: 50 nM; and ATP: 40 μM. The final concentrations of the test compounds ranged from 10 μM to 0.5 nM. The final concentration of each component in the JAK2/JAK3/Tyk2 reaction was: JAK2: 1 nM; substrate: 50 nM; and ATP: 10 μM. The final concentrations of the test compounds ranged from 10 μM to 0.5 nM. After the enzyme reaction ended, 5 μL of the 4× enzyme reaction termination solution was added into each well of the 384-well plate, centrifuged at 1000 rpm for 1 minute, and incubated at room temperature for 5 minutes. 5 μL of the 4× test antibody solution (final concentration of the test antibodies was 2 nM) was added into each well of the 384-well plate, centrifuged at 1000 rpm for 1 minute, and incubated at room temperature for 1 hour. After incubation of the antibodies, a signal value of each well was measured with Envision plate reader.

3. Data Analysis

Assuming that an inhibition rate of the enzyme solution blank control group was 100% and an inhibition rate of the negative control group (DMSO group) was 0%, an inhibition rate corresponding to each concentration was calculated. Nonlinear regression analysis was performed on the concentration logarithm values and corresponding percentage inhibition rates of the test compounds in GraphPad Prism software to obtain the half-maximum inhibitory concentrations ($IC_{50}$) of the test compounds. The test results measured for the compounds in Examples 1 to 10 are listed in Table 1 below.

TABLE 1

| No. | Tyk2/μM | JAK1/μM | JAK2/μM | JAK3/μM |
|---|---|---|---|---|
| TDM-180972 | 0.005 | 0.004 | 0.003 | 0.117 |
| TDM-180974 | 0.008 | 0.007 | 0.007 | 0.346 |
| TDM-180977 | 0.004 | 0.003 | 0.004 | 0.057 |
| TDM-180981 | 0.008 | 0.008 | 0.008 | 0.183 |
| TDM-180989 | 0.014 | 0.011 | 0.013 | 0.177 |
| TDM-180971 | 0.005 | 0.006 | 0.007 | 0.219 |
| TDM-180979 | 0.017 | 0.025 | 0.033 | 0.931 |
| TDM-180980 | 0.018 | 0.028 | 0.030 | >5 |
| TDM-180984 | 0.005 | 0.008 | 0.009 | 0.105 |
| TDM-180987 | 0.017 | 0.025 | 0.022 | 0.310 |

It can be seen from the results in Table 1 that the enzyme activity data of the compounds of the present disclosure are excellent, and the half-maximum inhibitory concentrations of the above specific compounds are relatively low, which are basically less than 0.03 μM for Tyk2, JAK1 and JAK2. The half-maximum inhibitory concentrations of compounds TDM-180972, TDM-180974, TDM-180977, TDM-180981, TDM-180971 and TDM-180984 are all less than 0.01 μM. Therefore, the experiments show that the small molecular compounds of the present disclosure are a class of compounds with strong targeting to the JAK family and excellent enzymatic activity, and can be used as JAK1/Tyk2 dual inhibitors and Tyk2 specific inhibitors.

The preferred embodiments of the present disclosure have been described in detail above. However, the present disclosure is not limited to the specific details in the above embodiments. Within the scope of the technical concept of the present disclosure, multiple simple modifications can be made to the technical solutions of the present disclosure, all of which fall within the claimed scope of the present disclosure.

It should also be noted that various specific technical features described in the above specific embodiments can be combined in any suitable way without contradiction. In order to avoid unnecessary repetition, various possible combinations are not described separately in the present disclosure.

In addition, any combination can be made among various embodiments of the present disclosure, as long as it does not depart from the concept of the present disclosure, which should also be regarded as being disclosed by the present disclosure.

What is claimed:

1. A small molecule compound, wherein the small molecule compound is a compound represented by Formula I, or a stereoisomer, a geometric isomer, a tautomer, a hydrate, a solvate, a pharmaceutically acceptable salt or a prodrug thereof:

[Formula I]

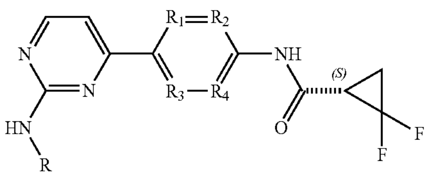

wherein $R_1$ to $R_4$ are each independently selected from C or N; and wherein R has a structure represented by Formula II below:

[Formula II]

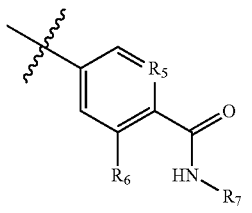

wherein $R_5$ is selected from C or N;

wherein $R_6$ is selected from hydrogen, halogen, an alkyl group, an amino group, an amido group, a cycloalkyl group, a heterocycloalkyl group, an aryl group, or a heteroaryl group; and wherein $R_7$ is selected from hydrogen, an alkyl group, a cycloalkyl group, a heterocycloalkyl group, an aryl group, or a heteroaryl group.

2. The small molecule compound according to claim 1, wherein at most two of $R_1$ to $R_4$ are N.

3. The small molecule compound according to claim 1, wherein $R_6$ and $R_7$ are each independently selected from hydrogen, an alkyl group, or a cycloalkyl group.

4. A small molecule compound, wherein the small molecule compound is a compound represented by Formula I below, or a stereoisomer, a geometric isomer, a tautomer, a hydrate, a solvate, a pharmaceutically acceptable salt or a prodrug thereof,

[Formula I]

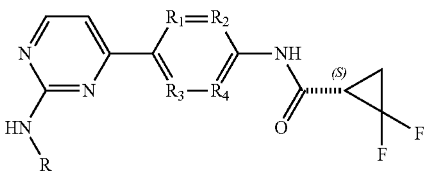

wherein $R_1$ to $R_4$ are each independently selected from C or N; and wherein R has a structure represented by Formula III:

[Formula III]

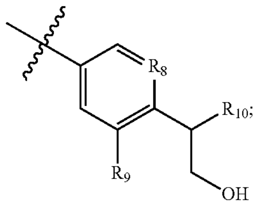

wherein $R_8$ is selected from C or N;

wherein $R_9$ is selected from hydrogen, halogen, an alkyl group, an amino group, an amido group, a cycloalkyl group, a heterocycloalkyl group, an aryl group, or a heteroaryl group; and wherein $R_{10}$ is selected from hydrogen, an alkyl group, a cycloalkyl group, a heterocycloalkyl group, an aryl group, or a heteroaryl group.

5. The small molecule compound according to claim 4, wherein $R_9$ and $R_{10}$ are each independently selected from hydrogen, an alkyl group, or a cycloalkyl group.

6. The small molecule compound according to claim 3, wherein the alkyl group is a methyl group, an ethyl group, a propyl group, or an isopropyl group, and the cycloalkyl group is a cyclopropyl group, a cyclobutyl group, or a cyclopropylmethyl group.

7. A method for inhibition of JAK kinase using the small molecule compound according to claim 1.

8. A method for prevention or treatment of an autoimmune disease and an immune-related inflammatory skin disease using the small molecule compound according to claim 1, wherein pathogenesis of each of the diseases is associated with a disorder in JAK signaling.

9. The method according to claim 8, wherein the autoimmune disease is at least one selected from the group consisting of rheumatoid arthritis, ankylosing spondylitis, ulcerative colitis, Crohn's disease, systemic lupus erythematosus, dermatomyositis, multiple sclerosis, type I diabetes mellitus, Sjogren's syndrome, and vasculitis.

10. The method according to claim 9, wherein the immune-related inflammatory skin disease is at least one selected from the group consisting of atopic dermatitis, eczema, alopecia areata, psoriasis, vitiligo, lichen planus, lichen nitidus, lichen sclerosus et atrophicus, panniculitis, acne, and hidradenitis suppurativa.

11. The small molecule compound according to claim 5, wherein the alkyl group is a methyl group, an ethyl group, a propyl group, or an isopropyl group, and the cycloalkyl group is a cyclopropyl group, a cyclobutyl group, or a cyclopropylmethyl group.

12. The small molecule compound according to claim 4, wherein at most two of $R_1$ to $R_4$ are N.

13. A method for inhibition of JAK kinase using the small molecule compound according to claim 5.

14. A method for prevention or treatment of an autoimmune disease and an immune-related inflammatory skin disease using the small molecule compound according to claim 4, wherein pathogenesis of each of the diseases is associated with a disorder in JAK signaling.

15. The method according to claim 14, wherein the autoimmune disease is at least one selected from the group consisting of rheumatoid arthritis, ankylosing spondylitis, ulcerative colitis, Crohn's disease, systemic lupus erythematosus, dermatomyositis, multiple sclerosis, type I diabetes mellitus, Sjogren's syndrome, and vasculitis.

16. The method according to claim 14, wherein the immune-related inflammatory skin disease is at least one selected from the group consisting of atopic dermatitis, eczema, alopecia areata, psoriasis, vitiligo, lichen planus, lichen nitidus, lichen sclerosus et atrophicus, panniculitis, acne, and hidradenitis suppurativa.

17. The small molecule compound according to claim 1, wherein $R_1$ and $R_3$ are C; and $R_2$ and $R_4$ are each independently selected from C or N.

18. The small molecule compound according to claim 4, wherein $R_1$ and $R_3$ are C; and $R_2$ and $R_4$ are each independently selected from C or N.

* * * * *